United States Patent
Kline et al.

(10) Patent No.: US 10,964,414 B2
(45) Date of Patent: Mar. 30, 2021

(54) METHODS AND APPARATUS FOR SECURITY ENHANCED PORTABLE DATA STORE AND PROCESSOR FOR ALLOWING SECURE AND SELECTIVE ACCESS TO GENOMIC DATA

(71) Applicant: Genosecurity, LLC, Reston, VA (US)

(72) Inventors: Paul A. Kline, Washington, DC (US); Allan M. Weinstein, Potomac, MD (US)

(73) Assignee: GENOSECURITY, LLC, Reston, VA (US)

( * ) Notice: Subject to any disclaimer, the term of this patent is extended or adjusted under 35 U.S.C. 154(b) by 0 days.

(21) Appl. No.: 15/429,814

(22) Filed: Feb. 10, 2017

(65) Prior Publication Data

US 2017/0235971 A1    Aug. 17, 2017

Related U.S. Application Data

(60) Provisional application No. 62/294,645, filed on Feb. 12, 2016.

(51) Int. Cl.
| | | |
|---|---|---|
| *G06F 21/62* | (2013.01) | |
| *G16H 10/60* | (2018.01) | |
| *G16B 30/00* | (2019.01) | |
| *G16B 50/00* | (2019.01) | |

(52) U.S. Cl.
CPC ......... *G16H 10/60* (2018.01); *G06F 21/6245* (2013.01); *G16B 30/00* (2019.02); *G16B 50/00* (2019.02)

(58) Field of Classification Search
CPC .... G06F 21/6245; G06F 19/321; G06F 19/18; G06F 19/322
USPC ......................................................... 713/193
See application file for complete search history.

(56) References Cited

U.S. PATENT DOCUMENTS

| | | |
|---|---|---|
| 8,806,127 B2 | 8/2014 | Brownell et al. |
| 8,837,718 B2 | 9/2014 | Lauter et al. |
| 9,087,216 B2 | 7/2015 | LaFever et al. |
| 9,202,066 B2 | 12/2015 | Sinderbrand et al. |
| 9,256,762 B1 | 2/2016 | Roth et al. |

(Continued)

FOREIGN PATENT DOCUMENTS

WO    WO 2013/178801    12/2013

OTHER PUBLICATIONS

International Search Report and Written Opinion dated May 19, 2017 for International Application No. PCT/US2017/017392.

(Continued)

*Primary Examiner* — Teshome Hailu
(74) *Attorney, Agent, or Firm* — Cooley LLP

(57) ABSTRACT

In some embodiments, a device includes a memory and a processor. The memory is operatively coupled to the processor and configured to store encrypted personal data. The processor is configured to receive query and a personal identifier from a user. Based on the query, the processor further identifies and retrieves a portion of the associated encrypted personal data from the memory. Using the personal identifier, the processor produces decrypted personal data by decrypting a portion of the retrieved encrypted personal data. The processor is further configured to analyze the decrypted personal data to identify a result of the query. The result is sent to the user without sending the decrypted personal data.

20 Claims, 4 Drawing Sheets

(56) References Cited

U.S. PATENT DOCUMENTS

| | | |
|---|---|---|
| 2002/0083320 A1 | 6/2002 | Vatanen |
| 2003/0039362 A1 | 2/2003 | Califano et al. |
| 2003/0055824 A1 | 3/2003 | Califano |
| 2003/0086591 A1 | 5/2003 | Simon |
| 2006/0024733 A1 | 2/2006 | Wong et al. |
| 2006/0106646 A1 | 5/2006 | Squilla et al. |
| 2008/0014146 A1 | 1/2008 | Von Hoff et al. |
| 2009/0030884 A1* | 1/2009 | Pulfer .............. G06F 17/30705 |
| 2010/0121872 A1 | 5/2010 | Subramaniam |
| 2010/0246827 A1* | 9/2010 | Lauter ................ G06F 21/6209 380/278 |
| 2012/0185951 A1* | 7/2012 | Bauman .............. G06F 21/6245 726/30 |
| 2013/0287206 A1 | 10/2013 | Hattori et al. |
| 2013/0314208 A1 | 11/2013 | Risheq et al. |
| 2014/0180950 A1* | 6/2014 | Sinclair ............... G06F 21/6245 705/325 |
| 2014/0350968 A1* | 11/2014 | Hahn ................... G06Q 20/123 705/3 |
| 2015/0058997 A1* | 2/2015 | Lee ..................... G06F 9/45558 726/26 |
| 2015/0244779 A1* | 8/2015 | Fitzgerald ............... H04W 4/21 705/2 |
| 2015/0248525 A1 | 9/2015 | Ury et al. |

OTHER PUBLICATIONS

Extended European Search Report dated Sep. 23, 2019, for EP Application No. 17 750 841.3, filed on Feb. 10, 2017, 10 pages.

* cited by examiner

— METHODS AND APPARATUS FOR
SECURITY ENHANCED PORTABLE DATA
STORE AND PROCESSOR FOR ALLOWING
SECURE AND SELECTIVE ACCESS TO
GENOMIC DATA

CROSS-REFERENCE TO RELATED APPLICATIONS

This application claims priority to and the benefit of U.S. patent application Ser. No. 62/294,645, filed Feb. 12, 2016 and titled "Methods and Apparatus for Portable Data Store and Processor for Allowing Selective Access to Secure Genomic Data," which is incorporated herein by reference in its entirety.

BACKGROUND

The human genome controls the behavior of almost every cell in our body from conception until death. Within the past few decades, astonishing progress has been made in genetic research and genome sequencing that has begun to transform clinical practice. Protecting such sensitive data is important for this data to become widely used in practice. Without protection, this data can be used for criminal activity and/or can pose serious privacy concerns.

Systems exist to use genetic data for identification, screening, diagnoses and dosing based on pharmacogenetics. For example, the U.S. Food and Drug Administration (FDA) approved a cytochrome P450 (CYP450) test called AmpliChip that can detect CYP2D6 and CYP2C19 polymorphisms. These two enzymes metabolize about a quarter of commonly prescribed drugs. The test can predict whether a patient is a slow or rapid metabolizer. Using this test, a patient taking a certain drug metabolized by these enzymes can avoid the tribulations of trial and error to find the correct therapeutic dose.

Systems also exist to predict the risk of acquiring a disease state. For example, the BRCA2 gene belongs to a class of genes known as human tumor suppressor genes. The protein produced from the BRCA2 gene helps cells control their rate of division, and is involved in the repair of damaged deoxyribonucleic acid (DNA). A mutation in this gene increases the risk of acquiring breast cancer as well as other cancers. Testing for a BRCA mutation uses a DNA sample from the patient, which is sent to a lab for analysis. This is a slow and inconvenient process.

Additionally, in some systems, a patient's entire genome can be sequenced and stored in a central database. A clinician then accesses the genetic database to determine the pharmacogenetics of a medication, or determine the disease risk for a patient. Such data centralization exposes patients' genomic data to the risk of data breaches and misuse.

SUMMARY

In some embodiments, a device includes a memory and a processor. The memory is operatively coupled to the processor and configured to store encrypted personal data. The processor is configured to receive a query and a personal identifier from a user. Based on the query, the processor further identifies and retrieves a portion of the associated encrypted personal data from the memory. Using the personal identifier, the processor produces decrypted personal data by decrypting a portion of the retrieved encrypted personal data. The processor is further configured to analyze the decrypted personal data to identify a result of the query. The result is sent to the user without sending the decrypted personal data.

DETAILED DESCRIPTION

Figure 1:
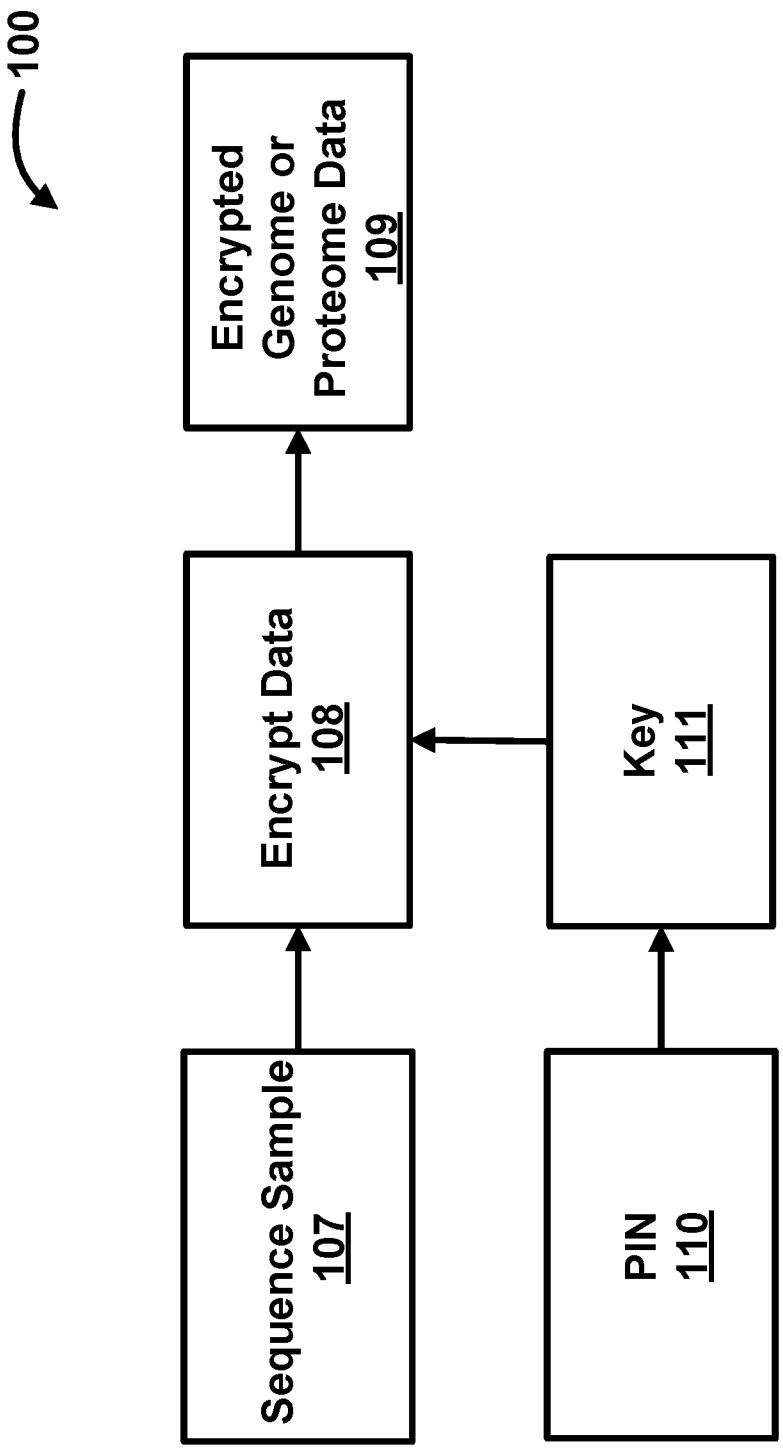
FIG. 1 is a schematic block diagram of a method of securely storing genomic and/or proteome data, according to an embodiment.

In some embodiments, a representation of a patient's genome, proteome and/or clinical records can be placed on an encrypted digital device that restricts or does not allow access to the information. A test or query can be run on the encrypted digital device, and the results of the test or query are reported to the user without reporting the underlying information, thereby protecting the representation of the patient's genome, proteome and/or clinical records. In other embodiments, a representation of the patient's genome and/or proteome can be placed on an encrypted digital device that does not allow a user (e.g., the patient or a third party) to access the information, but rather provides restricted information to another compute device to run a desired test or query, thus protecting the representation of the patient's genome, proteome and/or clinical records.

In some embodiments, a device includes a memory and a processor. The memory is operatively coupled to the processor and configured to store encrypted personal data. The processor is configured to receive a query and a personal identifier from a user. Based on the query, the processor further identifies and retrieves a portion of the associated encrypted personal data from the memory. Using the personal identifier, the processor produces decrypted personal data by decrypting a portion of the retrieved encrypted personal data. The processor is further configured to analyze the decrypted personal data to identify a result of the query. The result is sent to the user without sending the decrypted personal data.

In some embodiments, a method includes receiving, at a processor within a portable housing, a query and a personal identifier from a user. A portion of encrypted personal data associated with the query, stored in a memory within a portable housing, is identified by the processor. The portion of the encrypted personal data is retrieved from the memory in response to the query. The portion of the encrypted personal data conforms to a set of unmodifiable query restrictions. The portion of the encrypted personal data is decrypted using the personal identifier to produce decrypted personal data. The decrypted personal data is sent to the user.

In some embodiments, an apparatus includes a memory and a processor. The memory is operatively coupled to the processor and configured to store encrypted personal data. The processor is configured to receive a query from a user. Based on the query, the processor further identifies and retrieves a portion of the associated personal data from the memory. The processor is further configured to analyze the retrieved personal data to identify a result of the query. The result is then sent to the user without sending the personal data based on a set of unmodifiable query restrictions of the processor.

In some known systems, a patient's entire genome is sequenced and stored in a central database, which may be vulnerable to unwanted and malicious access. It is important to secure a patient's genetic data for privacy reasons, as well as to protect patients from potential criminal use of the genetic data. Systems described herein allow clinicians to use patients' genetic and/or proteomic information while protecting the patients' digital genetic and/or proteomic data. Some applications include the use of genetic and/or proteomic data to predict risk of diseases in the future, to diagnose disease states, and/or to assist a clinician in dosing a drug based on how a patient metabolizes the drug using pharmacogenetic data. In addition, encrypted data, such as medical record data, electronic medical records, lab data, medication history, radiographic information and/or the like, can be stored in a protected manner on the device.

In some embodiments, a personal genome or proteome device includes a communicator, a processor and a memory storing encrypted genomic and/or other personal data. The personal genome or proteome device isolates the data from outside devices. The data is stored in encrypted form in the memory and cannot be accessed by other devices except via the communicator. In some instances, the communicator and/or processor do not have privileges to copy entire blocks of data to another device. The communicator and/or processor can, however, access the data to provide medical data to another device. For example, if the requesting device sends a query to the communicator regarding the rate of metabolism for Warfarin™, the communicator and/or processor can access the genomic data at proper or relevant loci to determine the rate of metabolism. Such data is transferred to the communicator and/or processor in its encrypted form. The communicator and/or processor can decrypt the data using a key provided by the requesting device and determine the rate of metabolism based on such data. The rate of metabolism can be communicated to the requesting device, while the raw and/or underlying genome data is not accessible and thus not communicated. The personal data can include and is not limited to genomic data or proteomic data, electronic medical record information, for example, medical history, medical imaging, or medical laboratory results, and/or the like.

FIG. 1 is a schematic block diagram of a method of securely storing genomic or proteomic data, according to an embodiment. As shown in FIG. 1, a patient's sample is sequenced (107) and the sequenced genome or proteome data is encrypted (108) using a key (111) generated using a personal identifier such as, for example, a personal identification number (PIN) (110). A personal identifier can be unique for the patient, and can include a password (e.g., a multiple-digit alphanumeric sequence of characters, a username, and/or one or more biometric identifiers, such as fingerprints, facial recognition data, palm vein data, palm print data, hand geometry data, iris recognition data, retinal scans, scent detection data, etc.) The PIN (110) (or other personal identifier) can be provided by the patient or generated and provided to the patient. The encrypted data is stored (109) in a memory, which resides on a personal genome or proteome device. While described herein as being a PIN, in other instances any other suitable personal identifier (as described above) can be used instead of or in addition to a PIN. Thus, embodiments and/or implementations described herein as using a PIN can use any other suitable personal identifier instead of or in addition to a PIN.

Figure 2:
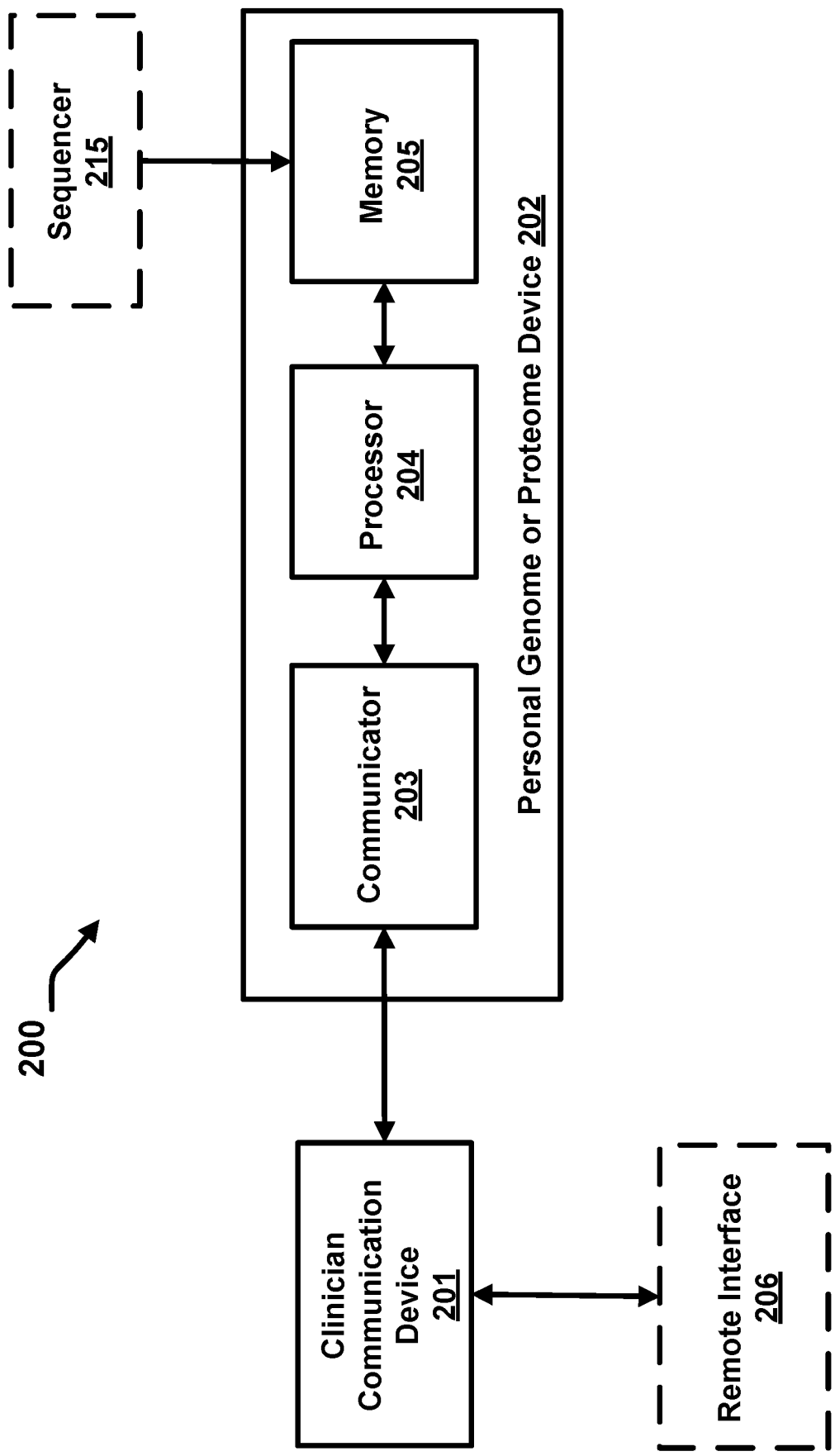
FIG. 2 illustrates a schematic block diagram of a personal genome or proteome device operatively coupled to a clinician communication device, a sequencer and a remote interface, according to an embodiment.

FIG. 2 is a schematic block diagram of a personal genome or proteome device, according to an embodiment. The personal genome or proteome device (202) includes a communicator (203), a processor (204), and a memory (205) storing encrypted data therein, which are collocated within a single portable device (e.g., a Universal Serial Bus (USB) drive, a chip dedicated to storing the data and installed in a mobile device such as a smart phone or a tablet, a chip dedicated to storing the data and installed on a card (e.g., a credit card form factor), etc.). The communicator (203) can include one or more of: an electrical port or connector configured to interface with a clinician communication device, a transmitter (e.g., an RF transmitter or an optical transmitter), a receiver (e.g., an RF receiver or an optical receiver), a cable, and an antenna. In some embodiments, the communicator (203) can also include a processor (e.g., an application-specific integrated circuit (ASIC), a general purpose processor, etc.) to perform functions such as decryption of genome data. In other embodiments, functions described herein as being performed by the communicator (203) can be performed by the processor (204). In some instances, the communicator (203) can also be referred to as a communication interface. In some implementations, the communicator (203), processor (204) and memory (205) are said to be collocated when arranged (or positioned) in the same portable housing. Further, an arrangement including, but not limited to, the communicator (203), processor (204) and memory (205) being part of the same Integrated Circuit (IC) (and/or even fabricated into a single Application Specific Integrated Circuit (ASIC)) can be considered collocated.

The processor (204) can be associated with a particular patient (also "user" or "owner"), and can be implemented using a microprocessor, such as, for example, an application-specific integrated circuit (ASIC), a central processing unit (CPU) with a non-modifiable memory (e.g., read-only memory (ROM)), a general purpose processor, etc. The processor can be "hard-wired" to perform some predetermined tasks and to be incapable of performing other predetermined tasks (e.g., to implement query restrictions). Specifically, rules to limit certain tasks can be implemented in hardware (e.g., in an ASIC or other processing device implementing hardware restrictions) or can be implemented in software executed in hardware (e.g., using instructions stored in a non-modifiable ROM). For example, the processor (204) can act as a "gatekeeper" that decrypts encrypted data of the memory (205) and controls access to that encrypted data. The processor (204) can be configured to implement rules (e.g., query restrictions), for example limiting access to a predetermined number of alleles per "session" (e.g., ≤100 alleles per session). As used herein, a "session" may be defined by chronological time (e.g., 24 hours), or by events (e.g., a session being initiated upon connection of the personal genome device (202) to the clinician communication device (201)), etc. As another example, the processor (204) can limit the number of loci searched and/or retrieved based on a sensitivity of a request (e.g., requests associated with more sensitive diseases, conditions and/or loci can be limited and/or restricted differently than requests associated with less sensitive diseases, conditions and/or loci). As yet another example, each loci and/or condition can be weighted based on a sensitivity and/or importance associated with that loci and/or condition and requests associated with multiple loci and/or conditions can be conducted up to a predetermined threshold. For example, a greater number of lower weighted loci (e.g., less sensitive loci) can be accessed during a time period than a number of higher weighted loci (e.g., more sensitive loci). Thus, the restrictions on access can be based on a sensitivity of the request. Prior to accessing and/or retrieving the portion of the encrypted data, the processor can analyze a received query to ensure the received query conforms to the set of query restrictions (or set of unmodifiable query restrictions). Such query restrictions can be implemented and/or enforced by the processor.

In some instances, different rules for accessing the data can be awarded to and/or associated with different PINs and/or users. The different rules for accessing and/or retrieving the data can be hardwired, partly configurable or fully configurable. These different rules together form one or more predetermined data access criteria. Prior to accessing and/or retrieving the data, the processor determines whether the amount of data accessed within a time period preceding the query has not met (or exceeded) a predetermined data access criterion related to a data access threshold. In another instance, prior to accessing and/or retrieving the data, the processor confirms whether the user access level associated with the user meets a predetermined access criterion associated with the portion of the encrypted personal data. For example, some users can perform a greater number of queries within a time period than other users. For another example, a threshold associated with a number of loci that can be accessed can be greater for users with a higher access level than users with a lower access level.

The memory (205) can include a non-volatile memory, such as read-only memory (ROM), programmable read-only memory (PROM), erasable programmable read-only memory (EPROM), electrically erasable programmable read-only memory (EEPROM) and/or the like. The memory (205) and/or the processor (204) includes processor-readable instructions for the processor (204) for the processing of test requests (e.g., queries) received, for example, via the communicator (203). The encrypted data stored in the memory (205) can include subgroupings of the patient's sequenced genome or proteome, without storing the entire sequenced genome or proteome. These subgroupings may be disease-specific. For example, the encrypted genetic data may include alleles or genes that are relevant to multiple sclerosis, breast cancer, prostate cancer, etc.

As shown in FIG. 2, a clinician communication device (201) sends a test request (e.g., in the form of a query) to a communicator (203). The test request can include, for example, a query to determine a metabolism type for a specified pharmaceutical drug for the patient, a query to determine whether a gene mutation, correlated with a disease such as cancer, is present in the patient's genome, or any other suitable query specific to the data stored in the memory (205). In some embodiments, the clinician communication device (201) can be computing device operated by a user (for example, a clinician, patient or an authorized third party) for providing at least a query or a personal identifier to the processor (204) via communicator (203).

The communicator (203) receives the test request and transmits the test request to the processor (204) to perform actions to respond to the test request. The processor (204) may parse and/or decode the test request before further processing. The further processing can include, for example, determining which loci of the encrypted genetic data stored in the memory (205) are relevant to the test request, such that those loci may be retrieved by the processor (204) from the memory (205). The further processing can also include, for another example, evaluating the test request to determine whether it is a valid request (e.g., to determine whether the test request is compliant with the query restrictions). For example, if generating a response to the test request would involve the processor (204) accessing a larger portion of the encrypted genetic data stored in the memory (205) than is permissible (e.g., too many loci) at the time that the test request is received, the processor (204) can categorize the test request as invalid and send a signal indicating that the test request is invalid or cannot be processed.

The processor (204) also receives the PIN used to unlock the data, validates the PIN, and queries the memory (205) for the data used to satisfy the query. In some implementations, the processor (204) receives the PIN from the clinician communication device (201) (e.g., entered into the clinician communication device (201) by the patient) via the communicator (203). For example, the PIN can be transmitted to the personal genome or proteome device (202) with the test request. In other implementations, the processor (204) receives the PIN via a user interface (e.g., a touchscreen, microphone, keypad, camera, electrical port, wireless antenna, etc.) of the personal genome or proteome device (202) (not shown in FIG. 2).

The data can be delivered to the processor (204) from the memory (205) in an encrypted form. In some instances, the processor (204) decrypts the data using the PIN or a key derived from the PIN, and performs actions to respond to the test request or query requested. In other words, the processor (204) can evaluate the decrypted genetic and/or proteomic data based on the test request, which may include comparing the decrypted data to a portion of the test request and/or to one or more lookup tables (e.g., stored in memory 205) associated with the test request. In addition, the processor may be used to decrypt clinical data using the PIN and to transfer the decrypted clinical data to the communicator (203).

The processor (204) reports the result to the communicator (203), which reports the result to the clinician communication device (201) (or user device, not shown in FIG. 2). The result can then be presented to the clinician and/or user on a display (not shown in FIG. 2) of the clinician communication device (201).

In some instances, as another security measure, the processor (204) can be restricted from being able to copy a large block of genetic data to curb the ability to illegally obtain the raw genetic data (e.g., as a query restriction). The restriction of the processor (204) from accessing "too much" genetic data (e.g., too many subgroupings during a given period of time or too many subgroupings being accessed simultaneously) can be implemented in software and/or hardware. For example, the processor (204) can be programmed to receive from the memory (205), and/or to process, a limited, predetermined volume of data per unit time. Alternatively or in addition, the processor (204) can include a local memory (e.g. processor-in-memory (PIM), first-in first-out (FIFO) memory, buffer) that is limited in size, or of which only a limited portion is available for temporarily storing data received from the memory (205) during processing. Alternatively, or in addition, the processor (204) can be programmed to receive from the memory (205), and/or to process, a limited, predetermined number of commands. Alternatively, or in addition, the processor (204) can be programmed to receive from the memory (205), and/or to process, a limited, predetermined number of blocks (e.g. alleles). Alternatively or in addition, the processor (204) can be an application-specific integrated circuit (ASIC) or other special-purpose microprocessor that is configured to enforce memory access restrictions. Alternatively or in addition, the memory (205) may only store a portion/subgrouping (or multiple portions/subgroupings) of the patient's sequenced genome, proteome, or other sensitive medical data at a given time, rather than a complete dataset.

In some implementations, the personal genome or proteome device (202) can include (e.g., be collocated with the communicator (203), the processor (204) and/or the memory (205)), or be operably coupleable to (e.g., via USB connection), a portable DNA sequencer (215) to collect replacement or additional genomic or proteomic data. The sequencer (215) can interface directly with a memory of the personal genome or proteome device (202) that is separate from or the same as a memory (205) that stores the encrypted data. In other embodiments, the sequencer (215) can interface with the memory of the personal genome or proteome device (202) via a network, intermediate device (e.g., clinician communication device (201)) and/or the like. A DNA sequencer (215) can be configured, for example, to collect one or more saliva and/or blood samples from the owner of the personal genome or proteome device (202) (i.e., the "user" or "patient"), and sequence DNA based on the collected sample(s) (for example, in 5 seconds or less). In other embodiments, the personal genome or proteome device (202) can include (e.g., be collocated with the communicator (203), the processor (204) and/or the memory (205)) or be operatively coupled to other types of data analyzers (not shown in FIG. 2) to receive other types of data (e.g., blood analyzers, saliva analyzers, tissue analyzers, bodily fluid analyzers, hair analyzers, stool analyzers, fingernail or toenail analyzers, cameras, pH sensors, urine analyzers, other sensors, etc.). These data analyzers can implement sophisticated techniques, involving use of sensors (such as bio-medical sensors), for sensing and/or processing the patient's physiological parameters to obtain data for analysis. In some instances, such data can be stored in memory (205) instead of or in addition to the genomic and/or proteomic data. In other instances, such data can be analyzed by processor (204) instead of, in addition to and/or in conjunction with the genomic and/or proteomic data to produce a result. In other instances, such data can be received from sources other than an analyzer included in or operatively coupled to the personal genome or proteome device (202) (e.g., can be received from other sources such as a networked or local database including such information) and stored in the memory (205).

For some diseases, such as neurofibromatosis type 1 (NF1), for example, twin siblings may exhibit identical genomes but have differing phenotypes. In such cases, to monitor NF1 in the affected sibling over time, protein tracking can be more effective than tracking the genome itself. As such, alternatively or in addition to genomic sequence data, the memory (205) can include proteome data and/or blood test results. As with the genetic data, the proteome data and/or the blood test results can be accessed by the processor (204) in response to performing actions and/or functions, by the processor (204), to respond to a test request received via the communicator (203). In some such implementations, the processor can process test requests to which responding involves the retrieval of proteome data and/or blood test results data from the memory (205) but not the retrieval of genetic data. In other such instances, test requests can include "combination" test requests, and the processor can process the combination test requests by retrieving genetic data as well as proteome data and/or blood test results data. In some implementations, the processor (204) is configured to encrypt the pattern of protein pathways and run queries against one or more nodes in that pathway. In other instances, any other suitable type of data (e.g., demographic data, medical record data, electronic medical records, lab data, medication history, radiographic information, etc.) can be stored on the personal genome or proteome device (202) and used in queries sent to the personal genome device (202).

In some implementations, the remote interface (206) can be a computing system with communication capabilities (wired and/or wireless) including but not limited to, for example, Ethernet, wireless Ethernet, radio frequency (RF) transceiver or optical transceiver (e.g., Bluetooth and/or near field communication (NFC)) to communicate with a clinician communication device (201), and/or the like. The remote interface (206) can be a handheld, portable device (such as mobile phone) or a computer (such as a desktop) and can be operated by a clinician and/or a user (e.g. the patient or an authorized third party) possessing valid credentials (e.g., login PIN, required passwords, etc.). For example, a clinician situated in a location remote to the clinician communication device (201), using his handheld device, may initiate a genome data request for a patient. The genome data request is received at the personal genome or proteome device (202) through a communication network (not shown in FIG. 2) using electrical signals or electromagnetic waves (e.g., the telephone network, the radio broadcasting system, computer networks and/or the Internet). The genome data request can include, for example, a query associated with the data stored in the memory and a valid credential (for example, a personal identifier (PIN)). This can allow a user and/or clinician to access the personal genome or proteome device (202) remotely via a network.

An example implementation, described with reference to FIG. 2, is as follows: if a clinician desires to start a patient on Warfarin™, the patient can provide the patient's personal genome or proteome device (202) to the clinician. The personal genome or proteome device (202) can be connected to the clinician communication device (201). The patient enters the PIN (e.g., via the clinician communication device and/or via a user interface, as discussed above). The clinician requests (via a test request) the proper Warfarin™ dosing via the clinician communication device (201) or, optionally, via a remote interface (206). The communicator (203) receives the test request from the clinician communication device (201) or remote interface (206), and the communicator (203), in turn, sends the test request to the processor (204) for processing (i.e., to provide the proper Warfarin™ dosing for the patient). Specific loci (e.g., CYP2C9, CYP4F2 and VKORC1) for determining a response to the test request can be specified in the test request itself, or can be determined via the processor (204), for example using a lookup table that includes one or more test requests/queries and their associated genetic indicators (e.g., loci). In the case of determining the proper Warfarin™ dosing based on a patient's Warfarin™ metabolism type, the processor (204) obtains genetic data from the CYP2C9, CYP4F2 and VKORC1 loci stored in the memory (205) and decrypts the genetic data from these loci (e.g., using the PIN or a key derived from the PIN). The processor (204) uses the decrypted genetic data to determine if the patient is a slow, intermediate or fast metabolizer of the drug based upon whether a variant allele is present at one or more of the specified loci. For example, CYP2C9*1 metabolizes Warfarin™ normally, CYP2C9*2 reduces Warfarin™ metabolism by 30%, and CYP2C9*3 reduces Warfarin™ metabolism by 90%. Because Warfarin™ given to patients with *2 or *3 variants will be metabolized less efficiently, the drug will remain in circulation longer, so lower Warfarin™ doses are desirable to achieve anticoagulation.

The result of the processor's (204) determination regarding the patient's metabolism of Warfarin™ is communicated to the clinician (e.g., via the clinician communication device (201)), however, no genomic data is provided to the clinician. The clinician can use the result to prescribe the proper dose of Warfarin™ for this specific patient, thereby avoiding a trial-and-error process.

In some implementations, the processor (203) can be reprogrammed to access different loci within the memory (205) and/or to analyze such data with different queries or reloadable algorithms. The processor (203) is restricted, however, from reading large blocks of genetic data from the encrypted genetic data of the memory (205) (these restrictions being implemented via software and/or hardware, as discussed above), and/or from reporting such raw data to the communicator (203). This prevents the personal genome or proteome device (202) from providing raw genetic data to a user even in the event of illegal or unauthorized processor (204) reprogramming. As discussed above, such rules can be implemented in hardware (e.g., in an ASIC or other processing device) or can be implemented in software executed in hardware (e.g., using instructions stored in a non-modifiable ROM). The processor is configured to suspend the sending of decrypted personal data to the user based on at least one of the hardware restrictions of the processor or instructions stored in memory (software executed in hardware).

In some instances, the memory (205) includes data for an entire single sequenced genome of a user/patient. In other instances, the memory (205) includes data for a subset of a single sequenced genome of a user/patient. In still other instances, the memory (205) includes multiple copies of genomic or proteomic data (e.g., multiple copies of the patient's entire genome or multiple copies of subgroupings thereof), for example to capture temporal changes in the patient's genomic data. Each copy of the multiple copies can correspond to a particular date and time, and be stored as such. In other words, the personal genome or proteome device may be "updated" over time, either by importing new sequenced genome data (as shown and described with reference to (107) of FIG. 1) or by direct testing via the sequencer (215). When the personal genome device has been updated with multiple temporal copies of the patient's genetic or proteomic data (or portion thereof), the processor (204) can process test requests based on comparisons between two or more of the temporal copies.

As discussed above, in some instances, the encrypted data of the memory (205) can include subgroupings of the patient's sequenced genome, rather than the entire sequenced genome. These subgroupings may be disease-specific. For example, the encrypted genetic data may include alleles or genes that are relevant to multiple sclerosis, breast cancer, prostate cancer, etc.

In some implementations, the personal genome or proteome device (202) does not include a transceiver, and is thus incapable of establishing a wireless connection with any external device. In other implementations, the personal genome device (202) includes a *radio* frequency (RF) or optical transceiver (e.g., Bluetooth and/or near field communication (NFC)), for example to communicate with a clinician communication device (201), to receive patient PIN data, to receive genetic data updates, etc.

While described above as restricting access to any raw and/or underlying genetic or proteomic data stored in the memory (205), in other embodiments the processor (204) allows some raw and/or underlying genetic or proteomic data to be provided to the clinician communication device (201). For example, based on certain queries, certain specific loci related to that query may be provided, but unrelated loci may be restricted from being provided. For another example, the processor (204) can be restricted to provide raw and/or underlying genetic and/or proteomic data for only a specific known query and/or purpose. In such an example, if raw and/or underlying genetic data is requested without an indication of a known query and/or purpose (e.g., as indicated by an indicator stored in a table and/or database accessible by the processor (204)), such raw and/or underlying genetic or proteomic data will not be returned. In other instances, the processor (204) can restrict the amount of raw and/or underlying genetic data that can be returned to the clinician communication device (201) based on a predetermined amount of raw and/or underlying genetic data per session, a predetermined amount of raw and/or underlying genetic data per a time period, a predetermined amount of raw and/or underlying genetic data based on a role associated with the clinician as indicated by a PIN provided to the personal genome or proteome device (202) (e.g., a doctor, a nurse, and/or a researcher may be able to access different amounts of raw and/or underlying genetic data) and/or any other suitable restrictions.

Figure 3:
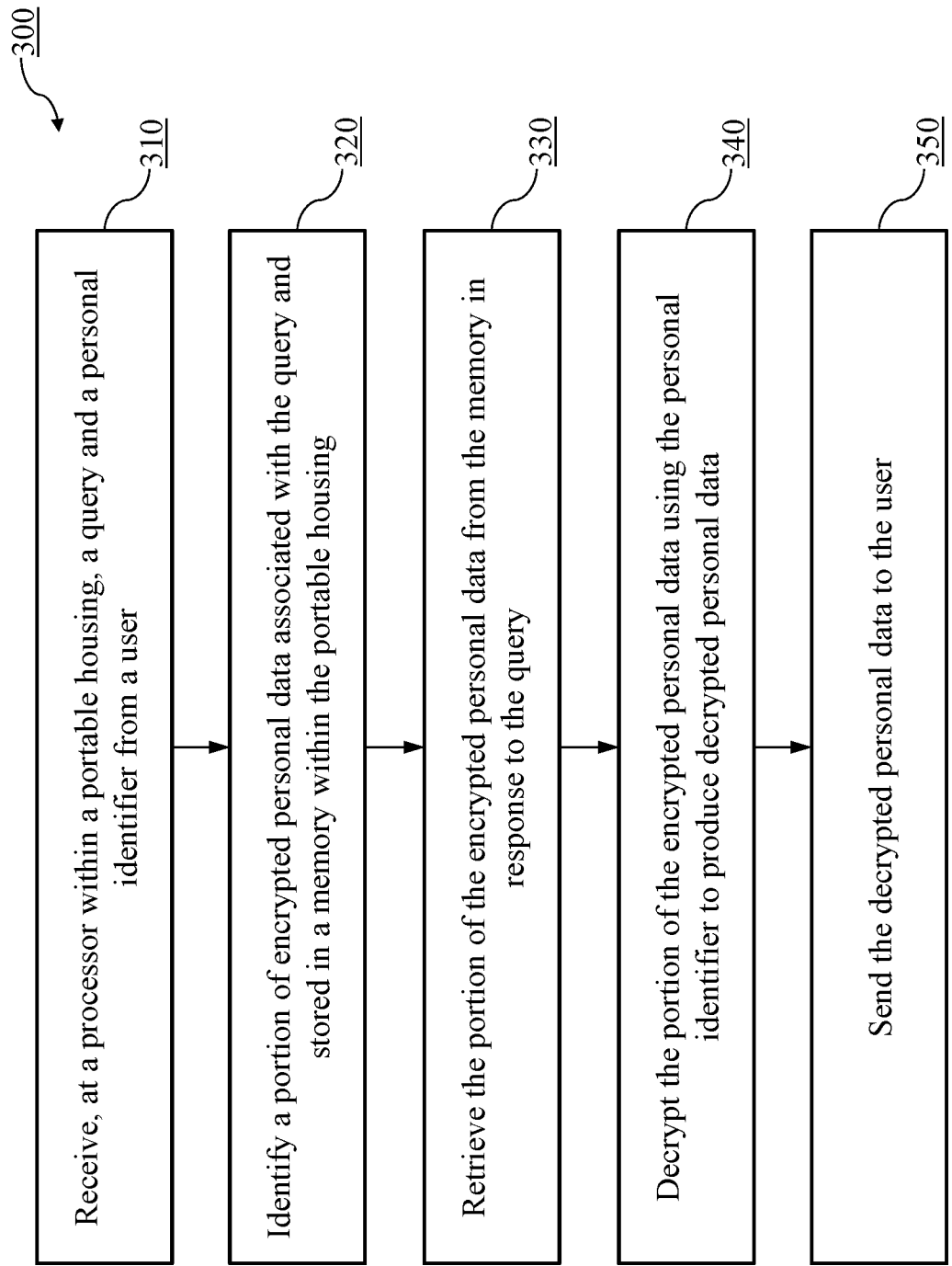
FIG. 3 is a flowchart of a method of securely storing genomic and/or proteome data, according to an embodiment.

FIG. 3 is a flowchart of a method 300 of securely storing genomic and/or proteome data, according to an embodiment. For example, the method 300 can be performed by the personal genome or proteome device (202) of FIG. 2.

At 310, the method 300 includes receiving a query and a personal identifier from a user at a processor within a portable housing. For example, the personal genome or proteome device (202) of FIG. 2 can receive a query and/or a personal identifier from the clinician communication device (201). The user (for example, a clinician, patient or an authorized third party) provides the query and/or the personal identifier to the processor (204) via clinician communication device (201). In some implementations, the user (for example, a clinician, patient or an authorized third party) can provide a personal identifier via a user interface (e.g., a touchscreen, microphone, keypad, camera, electrical port, wireless antenna, etc.) of the personal genome or proteome device (202) (not shown in FIG. 2). This can be instead of or in addition to a user providing the personal identifier to the processor (204) via clinician communication device (201). In some instances, for example, a clinician can provide a personal identifier via the clinician communication device (201) and a patient can provide a personal identifier via the user interface of the personal genome or proteome device (202).

At 320, a portion of encrypted personal data associated with the query and stored within the portable housing is identified. For example, the personal genome or proteome device (202) of FIG. 2 identifies a portion of encrypted personal data associated with and/or relevant to the received query stored in the memory (205) within the personal genome or proteome device (202). The portion of data associated with the query can answer a question posed by the query (e.g., either directly or indirectly).

At 330, in response to the query, the portion of the encrypted personal data is retrieved from the memory. For example, the personal genome or proteome device (202) of FIG. 2 retrieves the portion of the encrypted personal data from the memory (205) in response to the received query.

At 340, using the personal identifier, the portion of the encrypted personal data is decrypted to produce decrypted personal data. For example, the personal genome or proteome device (202) of FIG. 2 decrypts the portion of the encrypted personal data using the personal identifier (e.g., as a decryption key or as a seed or salt used to derive a decryption key) to produce decrypted personal data.

At 350, the decrypted personal data is sent to the user in the instance of a direct query. For example, the personal genome or proteome device (202) of FIG. 2 sends the decrypted personal data to the clinician communication device (201). The data is produced and sent over to the user through the clinician communication device (201) after the received query, requesting encrypted personal data at the processor (204), conforms to a set of unmodifiable query restrictions.

In some instances and as indicated in FIG. 3, the result (or answer) of a direct query can represent the decrypted and unmodified data. In the case of a direct query, the processor (204) can decrypt the portion of the data associated with the query and then send the decrypted data without modification to the requester (for example, clinician, patient and/or authorized third party). For example, if a clinician requests data representing a portion of the medical record data, the processor (204) can identify and retrieve from the memory (205) the portion of the corresponding encrypted medical record data associated with the requested query. After decrypting the identified medical record data, the processor (204) can send the decrypted medical record data to the requester without modification.

In other instances, the result (or answer) of an indirect query can include further processing (or calculation(s)) of the identified data portion to produce a desired result. In the case of an indirect query, the processor can decrypt the data and then perform further processing (or further calculation(s)) on the data to produce the desired result. The result can then be sent to the requester (for example, clinician, patient and/or authorized third party). For example, if the request is for determining the proper Warfarin™ dosing based on the patient's Warfarin™ metabolism type, the processor can identify the portion of the data used for determining Warfarin™ dosing. Based on the further processing (or calculations) of the identified data, Warfarin™ dosage is determined and the result is communicated to the requester (for example, clinician, patient and/or authorized third party) without providing any raw and/or underlying genomic data to the requester.

Figure 4:
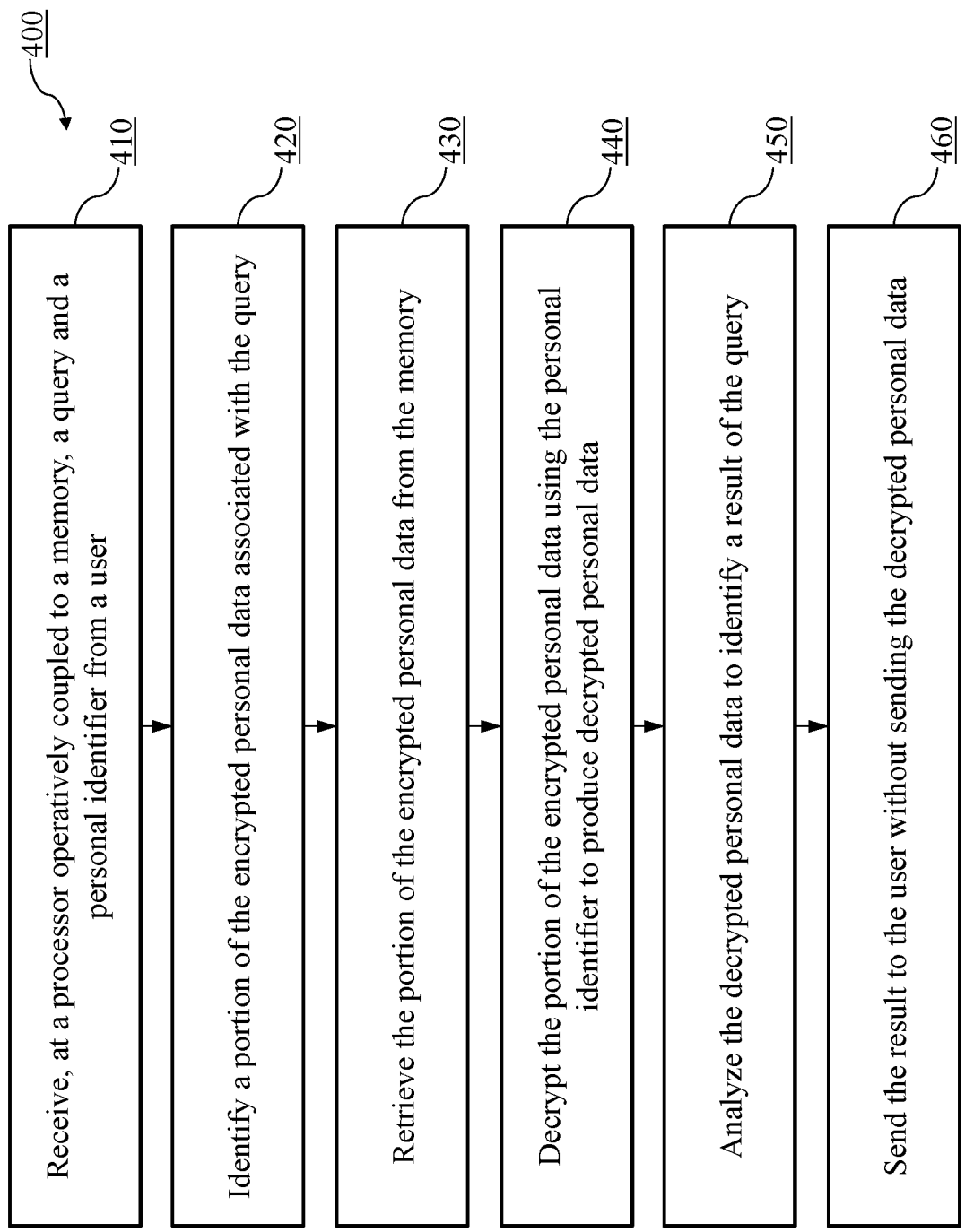
FIG. 4 is a flowchart of a method of securely storing genomic and/or proteome data and sending the result to the user without sending the decrypted personal data, according to another embodiment.

FIG. 4 is a flowchart of a method 400 of securely storing genomic and/or proteomic data and sending the result to the user without sending the raw and/or underlying decrypted personal data, according to another embodiment. For example, the method 400 can be performed by the personal genome or proteome device (202) of FIG. 2.

At 410, the method 400 includes receiving a query and a personal identifier from a user at a processor operatively coupled to a memory. For example, in FIG. 2, the personal genome or proteome device (202) that includes memory (205) can receive a query and/or a personal identifier from the clinician communication device (201). The user (for example, a clinician, patient or an authorized third party) provides the query and/or the personal identifier to the processor (204) via clinician communication device (201). In some implementations, the user (for example, a clinician, patient or an authorized third party) can provide a personal identifier via a user interface (e.g., a touchscreen, microphone, keypad, camera, electrical port, wireless antenna, etc.) (not shown in FIG. 2) of the personal genome or proteome device (202). This can be instead of or in addition to a user providing the personal identifier to the processor (204) via clinician communication device (201). In some instances, for example, a clinician can provide a personal identifier via the clinician communication device (201) and a patient can provide a personal identifier via the user interface of the personal genome or proteome device (202).

At 420, a portion of encrypted personal data associated with the query is identified. For example, in FIG. 2, the personal genome or proteome device (202) identifies a portion of encrypted personal data associated with the received query. Based on the received query, a portion of encrypted data can be identified by implementing genomic (or proteome) data comparing operations including but not limited to searching for non-exact genomic data matches stored in the memory (205). Other implementations may implement different mathematical-model-based techniques for the identification of the encrypted data. In another embodiment, specific loci (e.g., CYP2C9, CYP4F2 and VKORC1) for determining a response to the test request can be specified in the test request itself, or can be determined via the processor (204), for example using a lookup table that includes one or more test requests/queries and their associated genetic indicators (e.g., loci). The identification of the portion of the encrypted personal data is performed after the received query conforms to unmodifiable query restrictions and does not violate the predetermined data access criterion (e.g., query restrictions).

At 430, the portion of encrypted personal data is retrieved from the memory. For example, in FIG. 2, the personal genome or proteome device (202) retrieves the portion of encrypted personal data from the memory (205).

At 440, using the personal identifier, the portion of the encrypted personal data is decrypted to produce decrypted personal data. For example, in FIG. 2, the personal genome or proteome device (202) decrypts the portion of the encrypted personal data using the personal identifier to produce decrypted personal data.

At 450, the decrypted personal data is analyzed to identify a result of the query. For example, in FIG. 2, the personal genome or proteome device (202) performs an analysis on the decrypted personal data to identify a result of the query. The decrypted data is further subjected to analysis for determining the result. Consider a query received at the processor (204) for determining the proper Warfarin™ dosing based on a patient's Warfarin™ metabolism type. The decrypted data is analyzed by the processor (204) to determine if the patient is a slow, intermediate or fast metabolizer of the drug based upon whether a variant allele is present at one or more of the specified loci. For example, CYP2C9*1 metabolizes Warfarin™ normally, CYP2C9*2 reduces Warfarin™ metabolism by 30%, and CYP2C9*3 reduces Warfarin™ metabolism by 90%. Because Warfarin™ given to patients with *2 or *3 variants will be metabolized less efficiently, the drug will remain in circulation longer, so lower Warfarin™ doses are desirable to achieve anticoagulation.

At 460, the result is sent to the user without sending the decrypted personal data. For example, in FIG. 2, the personal genome or proteome device (202) sends the decrypted personal data to the clinician communication device (201) without sending the decrypted personal data. The decrypted personal data is produced and sent to the user via the clinician communication device (201) after the received query, requesting encrypted personal data at the processor (204), conforms to a set of unmodifiable query restrictions. For example, a requesting device (or clinician, patient and/or an authorized third party) can send a query to the personal genome or proteome device (202) regarding the rate of the metabolism for Warfarin™. The result of the personal genome or proteome device's (202) requested query is communicated to the requesting device (or clinician, patient and/or an authorized third party), however, no genomic data is provided. The clinician (and/or patient and/or an authorized third party) can use the result to prescribe the proper dose of Warfarin™ for this specific patient, without receiving the personal data.

While described above as storing genomic and/or proteomic data, in other instances the memory (205) can receive and/or store other data and/or information. The other information can include, for example, images, audio/video files, other types of media files and/or the like. The other information can also include, for example, complex software code such as certain algorithm(s), macro(s), batch files, pattern recognition algorithm and/or the like that can be used independently or in combination with data analyzers described above (not shown in FIG. 2) to aid in the result computation. The processor (204) can analyze data from the memory (205) and/or the result from the processor's (204) analysis of the data from the memory (205), with other data collected (e.g., from other sources such as other user-specific information, publicly available literature, research studies, known diagnoses and/or the like) to produce outcomes, diagnoses and/or recommendations using techniques involving (and/or related to) machine learning and/or artificial intelligence (AI). In other implementations, the processor (204) in addition to the memory (205) can also process the data obtained from an external memory device (not shown in FIG. 2) operatively coupled to the personal genome or proteome device (202) and/or sequencer (215). In another implementation, the other data can be stored in the memory (205), an external memory device (not shown in FIG. 2), and/or received from clinician communication device (201) and/or other device (e.g., such as a sensor and/or data analyzer as described above). Such machine learning and/or AI methods can be trained based on any known data such as on publicly available literature, research studies, known diagnoses and/or the like.

In another implementation, the clinician communication device (201) can transmit and/or receive data from the personal genome or proteome device (202) and analyze the received data with other data collected (e.g., from other sources) to produce outcomes and/or recommendations using techniques involving (and/or related to) machine learning and/or artificial intelligence (AI). The clinician communication device (201) is further capable of analyzing data from the personal genome or proteome device (202) with other data (or information such as other user-specific information, publicly available literature, research studies, known diagnoses and/or the like) collected from an external memory (not shown in FIG. 2) and/or data sources (not shown in FIG. 2) to produce outcomes, diagnoses and/or recommendations using techniques involving (and/or related to) machine learning and/or artificial intelligence (AI). For example, the clinician communication device (201) can determine the patient's Warfarin™ metabolism type based on additional details and/or factors such as age, ethnicity, gender and/or other similar personal parameter(s) received from sources other than the personal genome or proteome device 202. Such machine learning and/or AI methods can be trained based on any known data such as on publicly available literature, research studies, known diagnoses and/or the like.

While described above as including genomic data or proteomic data, electronic medical record information, medical history, medical imaging, or medical laboratory results, in other instances, the personal data stored in the memory (e.g., memory (205)) can include any type of data received from any type of data source (e.g., an analyzer, a scanner, a database (local or network connected), etc.). In some instances, for example, the personal data can include personally identifiable information (e.g., social security number, address, etc.), fingerprint information, financial information (e.g., bank account information, credit card information, etc.), age information, race information and/or the like. In such instances, queries can be made on such information similar to the queries described herein. Moreover, access restrictions can be placed on access to such data similar to the access restrictions described herein.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field-programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

What is claimed is:

1. An apparatus, comprising:
    a memory within a portable housing and configured to store encrypted personal data associated with an individual; and
    a processor within the portable housing and operatively coupled to the memory, the processor configured to:
        receive a query and a personal identifier from a user;
        identify a portion of the encrypted personal data associated with the query;
        retrieve the portion of the encrypted personal data from the memory;
        decrypt the portion of the encrypted personal data using the personal identifier to produce a decrypted portion of the encrypted personal data;
        analyze the decrypted portion of the encrypted personal data to identify a medical determination related to the individual in response to the query, the medical determination not including any part of either the decrypted portion of the encrypted personal data or the encrypted personal data; and
        send the medical determination to the user without sending any part of either the decrypted portion of the encrypted personal data or the encrypted personal data based on a set of predetermined query restrictions of the processor, the processor being hard-wired such that the set of predetermined query restrictions is unmodifiable by the individual,
        the encrypted personal data including a set of instances of the encrypted personal data, each instance from the set of instances representing the encrypted personal data at a different time than the remaining instances from the set of instances.

2. The apparatus of claim 1, wherein the encrypted personal data includes at least one of genomic data or proteomic data.

3. The apparatus of claim 1, wherein the encrypted personal data includes electronic medical record information including at least one of medical history, medical image data, or medical laboratory results.

4. The apparatus of claim 1, further comprising:
    a communication interface within the portable housing containing the memory and the processor, the processor configured to:
    receive the query and the personal identifier from the user via the communication interface; and
    send the medical determination to the user via the communication interface.

5. The apparatus of claim 1, wherein the processor is configured to encrypt unencrypted personal data using the personal identifier to produce the portion of the encrypted personal data prior to storing the portion of the encrypted personal data in the memory.

6. The apparatus of claim 1, wherein the processor is configured to determine that the query conforms to the set of predetermined query restrictions prior to retrieving the portion of the encrypted personal data from the memory.

7. The apparatus of claim 1, wherein the processor is configured to confirm, prior to retrieving the portion of the encrypted personal data from the memory, that an amount of data accessed within a time period preceding the query has not met a predetermined data access criterion.

8. The apparatus of claim 1, wherein the processor is configured to confirm, prior to retrieving the portion of the encrypted personal data from the memory, that a user access level associated with the user meets a criterion associated with the portion of the encrypted personal data.

9. The apparatus of claim 1, wherein the processor is configured to not send either the decrypted portion of the encrypted personal data or the encrypted personal data to the user based on the predetermined query restrictions of the processor.

10. The apparatus of claim 1, wherein the processor is configured to send the medical determination to the user via a computing device that analyzes the medical determination in conjunction with additional data to produce a recommendation.

11. The apparatus of claim 1, wherein the processor is configured to send the medical determination to the user via a computing device that uses artificial intelligence to analyze the medical determination in conjunction with at least one of publicly available literature, research studies or known diagnoses.

12. The apparatus of claim 1, wherein the processor is configured to receive the personal data from at least one of a DNA sequencer, a blood analyzer, a saliva analyzer, a tissue analyzer, a camera, a pH sensor, a bodily fluid analyzer, a hair analyzer, a stool analyzer, a fingernail analyzer, a toenail analyzer, or a urine analyzer, operatively coupled to the processor.

13. The apparatus of claim 1, wherein the encrypted personal data includes blood test data, and the medical determination is a blood test result.

14. The apparatus of claim 1, wherein the processor includes a rule, implemented using an application-specific integrated circuit (ASIC), to prevent modification of the set of predetermined query restrictions.

15. A method, comprising:
    receiving, at a processor within a portable housing, a query and a personal identifier from a user;
    identifying a portion of encrypted personal data associated with the query and stored in a memory within the portable housing,
        the portion of the encrypted personal data being a subset of the encrypted personal data stored in the memory, and
        the encrypted personal data associated with an individual;
    retrieving the portion of the encrypted personal data from the memory in response to the query, the portion of the encrypted personal data conforming to a set of predetermined query restrictions of the processor, the processor being hard-wired such that the set of predetermined query restrictions is unmodifiable by the individual;
    decrypting the portion of the encrypted personal data using the personal identifier to produce a decrypted portion of the encrypted personal data;
    analyzing the decrypted portion of the encrypted personal data to identify a medical determination related to the user in response to the query, the medical determination not including any part of either the decrypted portion of the encrypted personal data or the encrypted personal data, and
    sending the medical determination to the user without sending any part of either the decrypted portion of the encrypted personal data or the encrypted personal data, based on the set of predetermined query restrictions, the encrypted personal data including a set of instances of the encrypted personal data, each instance from the set of instances representing the encrypted personal data at a different time than the remaining instances from the set of instances.

16. The method of claim 15, wherein the set of predetermined query restrictions includes confirming that an amount of data accessed within a time period preceding the query has not met a predetermined data access criterion.

17. The method of claim 15, wherein the encrypted personal data includes at least one of genomic data or proteomic data.

18. The method of claim 15, wherein the encrypted personal data includes electronic medical record information including at least one of medical history, medical image data, or medical laboratory results.

19. The method of claim 15, further comprising:
confirming, prior to the retrieving, that a user access level associated with the user meets a criterion associated with the portion of encrypted personal data.

20. The method of claim 15, further comprising sending the medical determination to the user via a computing device that analyzes the medical determination in conjunction with additional data to produce a recommendation.

* * * * *